United States Patent [19]
Chen

[11] Patent Number: 5,958,451
[45] Date of Patent: Sep. 28, 1999

[54] PROCESS FOR PRODUCING POROUS, CONTROLLED-RELEASE CAPSULES AND ENCAPSULATED COMPOSITION

[75] Inventor: Gan-Lin Chen, Taipei, Taiwan

[73] Assignee: Yung Shin Pharm Ind. Co., Ltd., Taichung, Taiwan

[21] Appl. No.: 08/706,907

[22] Filed: Sep. 3, 1996

[51] Int. Cl.$^6$ ................................................. A61K 9/52
[52] U.S. Cl. ........................ 424/457; 424/451; 424/452; 424/456
[58] Field of Search .................... 424/466, 451, 424/456, 457, 452

[56] References Cited

U.S. PATENT DOCUMENTS

| | | | |
|---|---|---|---|
| 3,823,816 | 7/1974 | Controulis et al. | 206/5 |
| 4,609,403 | 9/1986 | Wittwer et al. | 106/122 |
| 4,719,112 | 1/1988 | Mayer et al. | 424/456 |
| 5,466,460 | 11/1995 | McMahon et al. | 424/408 |

OTHER PUBLICATIONS

Higuchi, Rate of Release of Medicaments from Ointment Bases Containing Drugs in Suspension, Journal of Pharmaceutical Sciences, vol. 40, p. 874, 1961.

Jain, et al., Design of a Slow–Release Capsule Using Laser Drilling, Journal of Pharmaceutical Sciences, vol. 73, No. 12, p. 1806, 1984.

Quigley et al., *Medline*, #92309153, 1993.

Graham, *Chemical Abstracts*, vol. 114, #49582, 1992.

Bauer et al., *Chemical Abstracts*, vol. 120, #194421, 1994.

Phadke et al., *Chemical Abstracts*, vol. 116, #241948, 1992.

*Primary Examiner*—Thurman K. Page
*Assistant Examiner*—James M. Spear
*Attorney, Agent, or Firm*—Smith, Gambrell & Russell, LLP; Beveridge, DeGrandi, Weilacher & Young Intellectual Property Group

[57] ABSTRACT

The porous capslues were prepared by mechanical drilling, addition of effervescent to gelatin solution, or purging of inert gas into the gelatin solution. The porous capsules were then hardened by exposure to the cross-linking reagent, or by radiating under the UV, or microwave, or γ-Ray. The usage of these porous gelatin capsules apart for pharmaceuticals extends to veterinary, cosmetic, and nutrient purposes. They are also utilized in the delivering of required beneficial agents to the chemical reactor, environment, and for agricultural purposes.

7 Claims, 4 Drawing Sheets

PROCESS FOR PRODUCING POROUS, CONTROLLED-RELEASE CAPSULES AND ENCAPSULATED COMPOSITION

BACKGROUND OF THE INVENTION

There are various routes of drug administration with orally administered drug accounting for about 70–80%. The dosage form for this route is convenient to use, has high therapeutic efficiency coupled with low side effects. Oral dosage forms include tablet, capsules, and other solids. Tablets are nonetheless widely used.

The emergence of controlled released dosage form during the 1940–1950 period offered long acting effect and with concomitant reduction of frequent administration of the drug. A range of drug delivery systems were developed from then on.

Orally controlled released dosage forms usually require the following:

1. Coating of active drug component with low soluble material which should be soluble in the GI tract.
2. Complexation or combination of drug with other components.
3. Drug interaction with ion exchange resins.
4. Mixing of drug with matrix.

Generally drugs have different physico-chemical properties depending primarily on the structure. Excipients like diluents, lubricants, maskers, disintegrants, binders or coloring materials and sweeteners are mixed with drugs for suitability and better oral dosage forms. Injectables dosage forms when used will not pass through the GI tract. Furthermore other dosage forms can be administered through the nose, implantation, transdermal, suppositories or for vaginal application to release the drug slowly.

T. Higuchi in *J. Pharm. Sci.* 40, 874(1961) tabletted drug, polymer, and other excipients into a matrix type by oral controlled tablet. This kind of controlled dosage form demands a very specialized and complicated manufacturing process. It also needs very special formulation to achieve optimal controlled effect.

A. G. Thombre invented the WPI Patent 94-199917124, controlled release delivery device special capsule containing Osmagent, coated macro-particulate solubility modifier, and active material in asymmetric membrane.

C. Camponeschi et al. invented the WPI Patent 94-169606/21, controlled release composition containing ursodeoxycholic acid. It consist of micro-granules prepared by extrusion-spheronisation containing the drug, a plasticiser, a binder, and optimal disintegrants.

K. L. Branly et al. invented the WPI Patent 93-312854/40, microcapsules with controlled release and improved handling safety-consisting of active core material (e.g. herbicide) encapsulated in glutaraldehyde cross-linked gelatin containing a water-soluble softener.

S. M. Herbig et al. invented the WPI Patent 92-079771/10, devices for controlled release of active agents e.g. drugs, nutrients -have shell comprising interfacially polymerised membrane on porous support surrounding core of active agent.

ELAN Corp. PLC have the WPI Patent 85-110586/19, oral granules for controlled release of methyidopa which comprises core containing acid and external polymeric membrane.

The use of laser to drill holes on drug controlled released system was reported by N. K. Jain in *J. Pharm. Sci.* 73, 1806(1984). The theory involved the usage of formaldehyde to make the gelatin capsules cross-linked and become GI tract insoluble capsules. The drug eventually will be released through the small holes in the capsule into the dissolution medium and this kind of controlled dosage forms have sustained release effect. The laser drilling on the capsule is not easy to orientate and achieve hence it can not be industrially employed or utilized.

DETAILED DESCRIPTION

SUMMARY OF THE INVENTION

This invention proposed is to provide porous gelatin capsules by using novel preparation methods.

The main objective of this invention is to provide porous gelatin capsules having a controlled released property.

Furthermore, this invention provides porous gelatin capsules which when filled with medical agents, agricultural chemicals, reaction chemicals and catalysts, cosmetics, nutrients, environment beneficial agents, the extracts of natural products, flavors, fragrances, coloring agents, or enzyme etc. have controlled released property that is independent of the type of drug or other beneficial agent enclosed.

BRIEF DESCRIPTION OF THE DRAWINGS

The invention will now be described in a more detailed form with reference to the accompanying drawing 5.

Table 1 The effects of exposure time of capsule to formalin on dissolution (verapamil as the model drug, water were used as dissolution medium, n=6)

Table 2 The effects of exposure time of capsule to formalin on dissolution (verapamil as the model drug, 0.1N HCl aq. solution were used as dissolution medium, n=6)

Table 3 Values of effervescent added, dissolution time period, slope of release, intercept of release, coefficient of determination, and release exponent of various dissolution data (verapamil as the model drug, water were used as dissolution medium, n=6)

Figure 1:
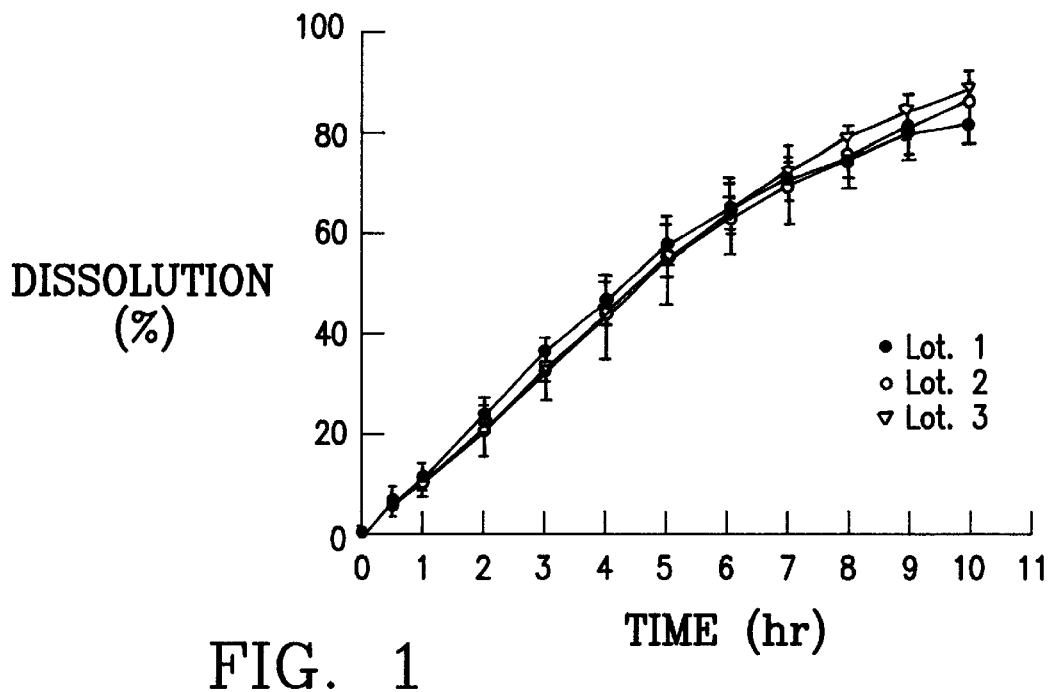

FIG. 1. Release of verapamil in starch as a function of time from porous capsules of three different lots (water as dissolution medium, n=6).

Figure 2:
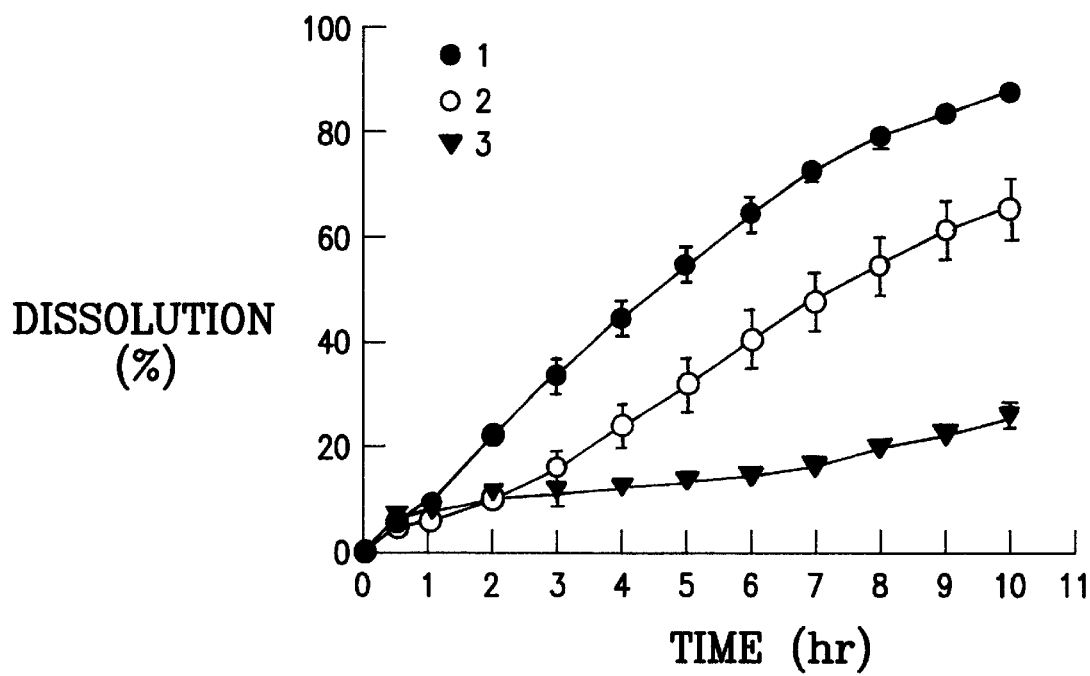

FIG. 2. Release of verapamil in starch as a function of time from porous capsules of different exposure time to formaldehyde (water as dissolution medium, n=6).

Key: exposure time of porous capsules to formaldehyde

| 1: 2 hrs | 2: 4 hrs | 3: 7 hrs |

Figure 3:
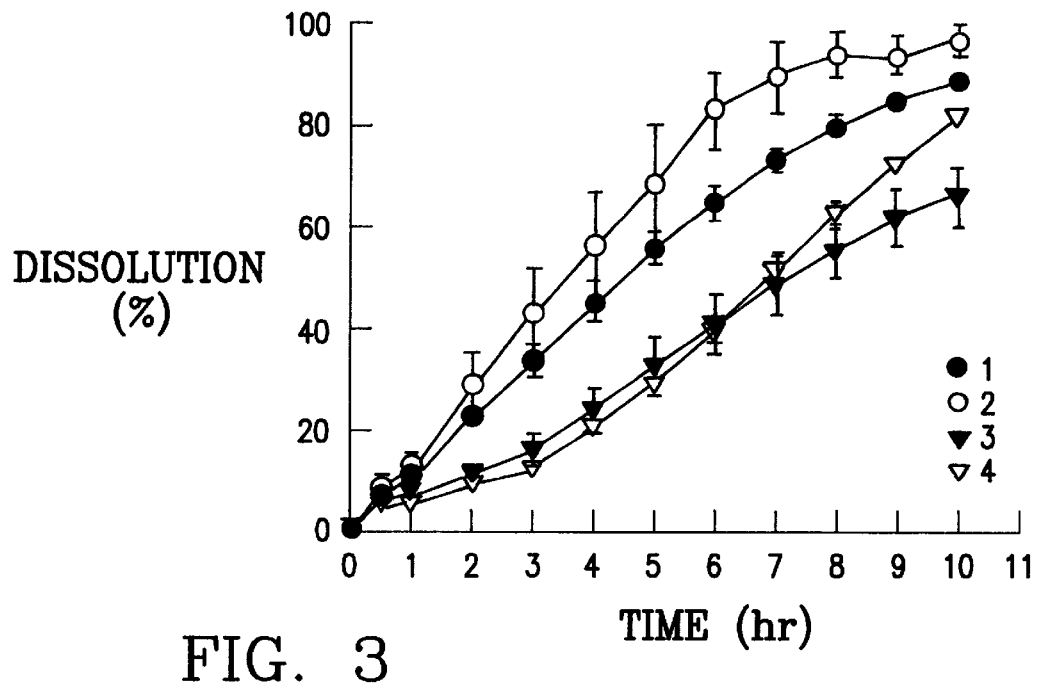

FIG. 3. The dissolution profiles of different dissolution medium and exposure time of porous capsule to formalin.

Key: dissolution medium/exposure time of porous capsules to formaldehyde

| 1: water/2 hrs | 2: 0.1N HCl/2 hrs |
| 3: water/4 hrs | 4: 0.1N HCl/4 hrs |

Figure 4:
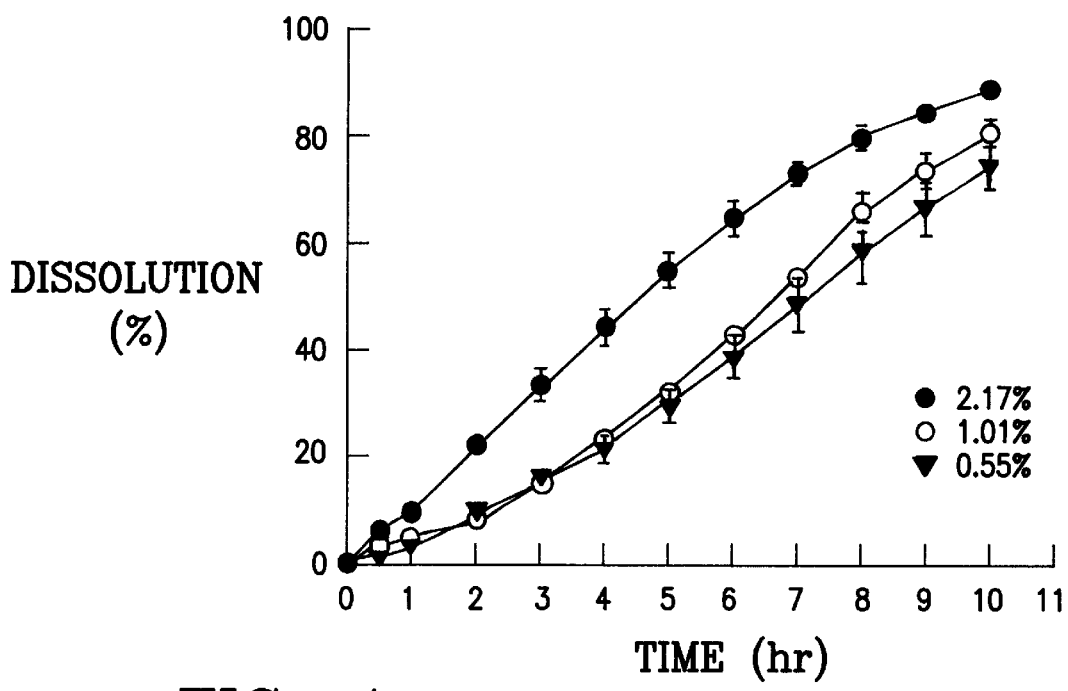

FIG. 4 Release of verapamil in starch as a function of time from porous capsule with the addition of different amounts of gas-generating reagent. (water as dissolution medium, n=6).

| 1: 2.17% | 2: 1.01% | 3: 0.55% |
|---|---|---|

Figure 5:
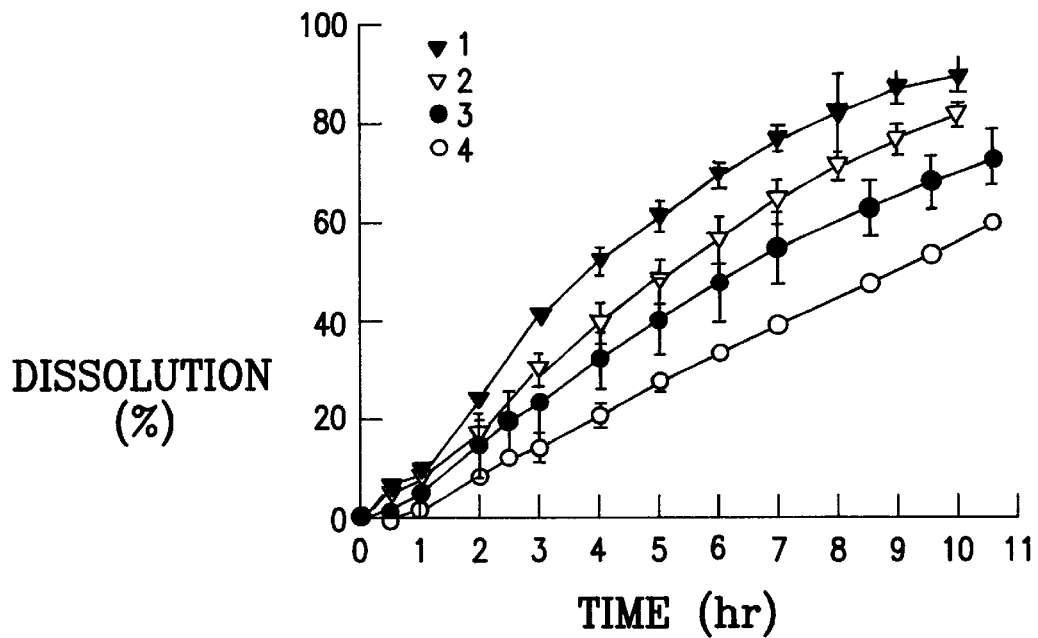

FIG. 5. Release of verapamil in starch as a function of time from conventional capsule which were drilled with various numbers of 0.9 mm pores and exposed to formalin for 2 hours (water as dissolution medium, n=6).

Key: numbers of 0.9 mm pores

| 1: 8 holes | 2: 6 holes | 3: 4 holes | 4: 2 holes |
|---|---|---|---|

Figure 6:
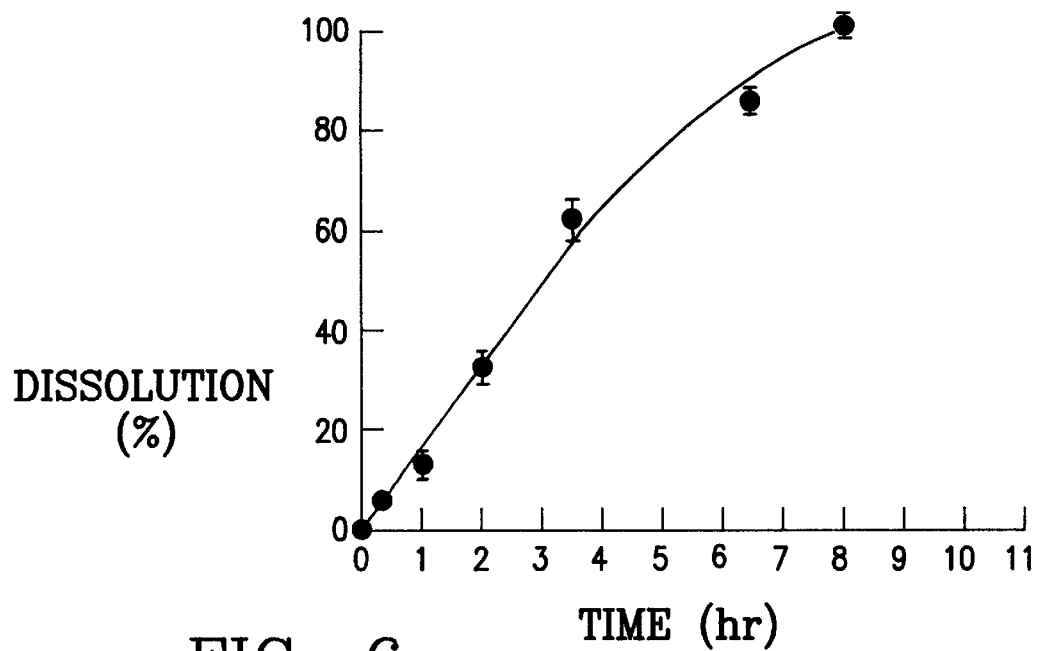

FIG. 6. Release of verapamil in starch as a function of time from porous capsules and exposed to microwave for 1 minute. (water as dissolution medium, n=6).

Figure 7:
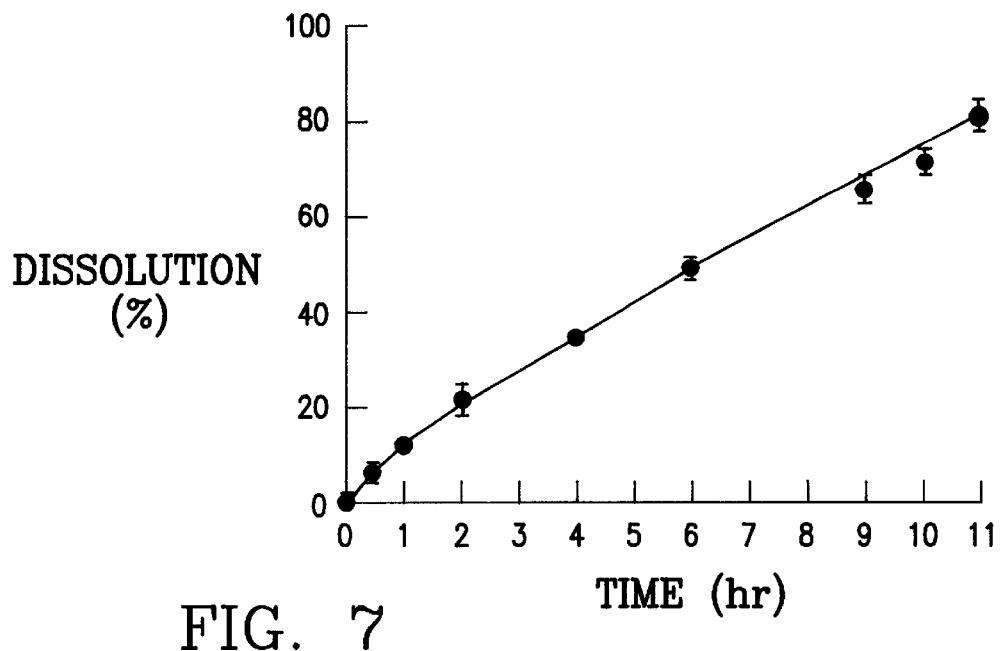

FIG. 7. Release of verapamil in starch as a function of time from porous capsules and exposed to 2 Mrads γ-Ray radation(water as dissolution medium, n=6).

Figure 8:
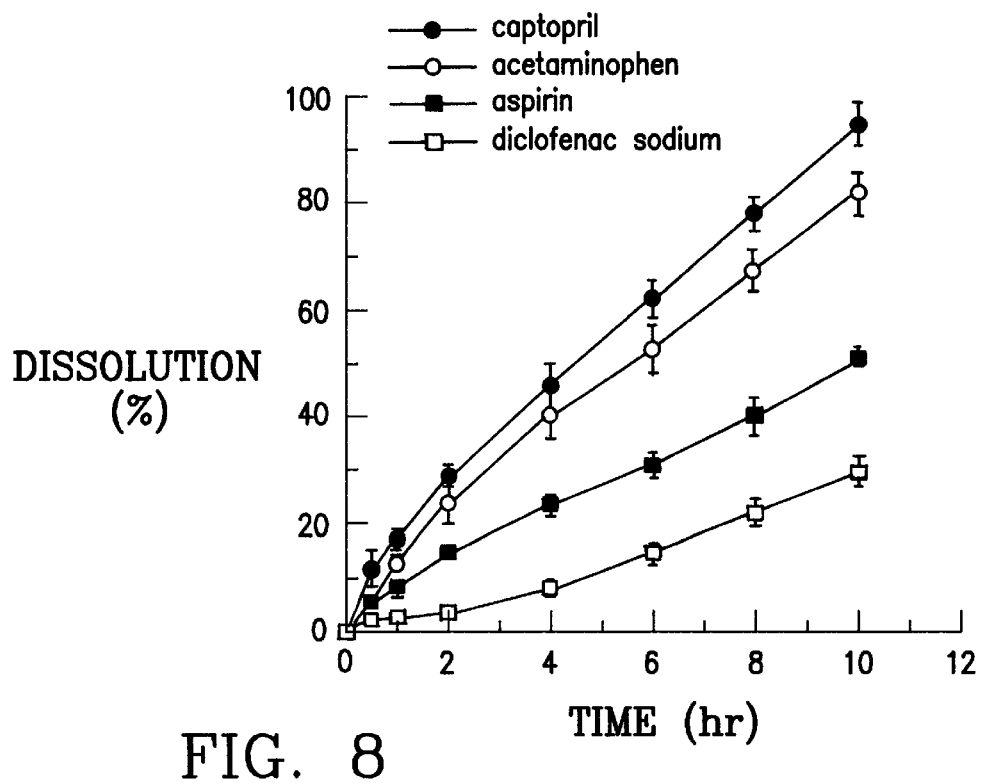

FIG. 8. Release of various drugs in starch as a function of time from porous capsule. (water as dissolution medium, n=6).

In this present invention, porous gelatin capsules could be made through:

Chemical method-effervescent addition into gelatin solution

Mechanical drilling method

Purging inert gas (or it's solid, liquid phases) into the gelatin solution.

The exposure of the capsules to formaldehyde, glutaraldehyde, or other cross-linking reagents such as: Denacol$^R$, EX-131(Methyl glycidyl ether), EX-810 (Ethylene, polyethylene glycol diglycidyl ether), EX-313 (Glycerol polyglycidyl ether), EX-512(Polyglycerol polyglycidyl ether), or the use of microwave, UV light, cobalt-60 or other type of radiation hardens the porous gelatin capsules.

This kind of porous capsule has a controlled released property that is independent of the type of drug or other beneficial agent enclosed. For example, the filling of some pharmaceutical composition, agricultural product, reaction chemicals and catalysts, cosmetics, nutrients, environment beneficial agents, the extracts of natural products, flavors, fragrances, coloring agents, or enzyme etc. into the porous capsule have demonstrated the controlled released property of these capsules.

Although the controlled released effect of porous capsule is independent of the chemico-physical property of the filling agents, this system still need excipients to enhance the controlled release effect of the active agents such as: medical agents, agricultural chemicals, reaction chemicals and/or catalysts, cosmetics, nutrients, environment beneficial agents etc. If necessary, the filling formulation wherein comprising active ingredients and expients like diluents, lubricants, disintegrants, maskers, binders or coloring materials and sweeteners etc. These active ingredients described above are, for example, verapamil HCl, captopril, acetaminophen, aspirin, diclofenac sodium, nicardipine HCl etc. with expients like starch, sugars, polymers etc. When filled with organophosphate, epoxide, fertilisers, herbicides, insecticides as active ingredients, and formulated with suitable excipients, then these devices became a controlled release agricultural composition. If this device was filled with nutrients or cosmetic agents: such as vitamins, extracts from natural products, and formulated with flavors, fragrances, binders, coloring agents, maskers, or other excipients etc. then these were formed as nutrient or cosmetic controlled release compositions. When the devices were filled with,insecticides, air fresheners,or other environment beneficial agents as active ingredients and expients like diluents, binders, coloring materials, or maskers etc. then these became an environmental controlled release composition. If this porous capsule were filled with reaction chemicals and/or catalysts which were needed in chemical engineering as active ingredients and combined with excipients, then these became industrial controlled release composition.

The procedures of manufacturin capsules are: (a) preparation of a gelatin solution (b) preparation of capsules in a molten states (c) cutting of the dried molten state (d) quality control and packaging.

This invention "Porous Capsule" no matter the met hod used-mechanical, chemical or purging by gas (or other phases such as solid and liquid forms), is how ever different from the conventionally known capsules.

The mechanical method of preparing these capsules involves the use of pin and mold with a hole of 0.1–2.0 mm in diameter and the number of insertions from 1–20. A special clip is then used to make insertions and subs equently detach the capsule produced.

Chemical method was utilized when gas gene rating agents such as a weak acid and a weak base were employed. In this method, gas was generated and was suspended on the capsule wall and hardened with exposure to formaldehyde.

Weak acids used include: citric acid, tartaric acid, fumaric acid, maleic acid etc. and weak bases used include: sodium carbonate, potassium carbonate, calcium carbonate, magnesium carbonate, lithium carbonate etc. The proportion of acid to base is usually acid: base (8:1 to 1:8, w/w) with the best formulation as acid: base (4:1 to 1:4, w/w). The total weight of the combined weak acid and base used is 0.1–10% of the total gelatin weight with the optimal properties was found to be 0.2–4.0% of the total gelatin weight.

When a gas is purged into the gelatin, inert gases which do not react with the gelatin capsules were used and are usually $CO_2$, $N_2$, He and other inert gases (or other phases such as solid and liquid forms) etc. The purge rate is 3–30 ml/second through a porous filter which exclusively stirs the gas thoroughly to reduce the size of the bubbles and maintain the homogeneous state of the gas. This ensure that the walls of the capsule are filled with normal sized bubbles.

The hardening process of the capsules maintains the appearance of the capsules. The known procedures use oxidant or radiation that could be employed as well in our invention. We used formaldehyde or glutaldehyde as hardening agent and it takes usually 0.1–6 hours to complete the hardening process. We used a dose of 1–5 Mrad generated from Co-60 or microwave operating at 400–1200 W, or UV light at 280–8000 $mJ/cm^2$.

Generally, the thickness of the wall of the capsule is determined by the viscosity of the gelatin solution, time and speed of dipping in and withdrawing the pin and mold. The viscosity of the gelatin invariably depends on the amount used and the temperature control. When the amount of gelatin used increases or the temperature decreases, the viscosity of the gelatin solution increases and vice versa. The excess amount of gelatin normally drips out by gravity. If the dipping time and withdrawal speed are too fast, this will result in thin capsule wall. The reverse is the case when the dipping time and withdrawal speed are too slow. In the manufacturing process, attention should be paid to a. Amount and viscosity of gelatin and b. Dipping time and withdrawal speed.

The moisture content is very important to the quality of the capsules and was generally controlled in the range of 12–15% of the total capsule weight. If moisture content is less than 10%, the capsule becomes brittle or shrink. This changes the capsule size and integrity and makes it difficult to fill the capsule with the required amount of drug. If the moisture content is higher than 16%, the gelatin becomes soft and loses its mechanical strength rendering it unsuitable in the capsule filling machine.

The optimal temperature of operation for producing these capsules should be 50–80° C. while the humidity should be less than 80% and the effervescent (or bubbling agent) in the range of 0.01–5.5%.

The formulation ratio of amount of gelatin used: distilled water: effervescent=30:60:2 was used to prepare the porous capsules. Formaldehyde is used to harden it before filling with verapamil hydrochloride: corn starch=1:4. FIG. 1 shows that different batches of capsules have no difference in drug release. The reproducibility of these capsules is good and confirms that the bubbles in these porous capsules are homogeneously distributed in the gelatin solution.

We used 1.17% w/w effervescent in gelatin solutions to make these porous capsules and filled them with verapamil HCl: starch=1:4. The amount of corn starch used was 180 mg. The capsules were exposed to formaldehyde at 2, 4 and 7 hours and then analyzed for their drug release profile.

When water is used as dissolution medium, the results are shown in FIG. 2. and the release parameters in Tab. 1. When the data were subjected to Korsmeyer model, the n value revealed that it is a zero order release. The drug release rate decreases as the formaldehyde exposure time increases. This indicates that the gelatin has high amount of cross-linkage.

When 0.1N HCl is used as dissolution medium, the results are shown in FIG. 3 while the regression parameters are shown in Tab. 2. From Krosmeyer model, we know that this is also a zero order drug release and drug release rate decreases as the exposure time to formaldehyde increases. However, under the same formaldehyde exposure time, 0.1N HCl dissolution n medium has slightly better release rate compared to water as dissolution medium.

Effervescent has effect on drug release rate apart from formaldehyde. FIG. 4 shows porous capsules with different amount of effervescent. The capsules were all treated with formaldehyde for 2 hours. Water was used as dissolution medium and the regression parameters are shown in Tab. 3. According to Krosmeyer equation, we know that it is a zero order release. The amount and size of bubbles generated were different essentially because of different amount of effervescent used.

From the FIG. 4 and Tab. 3 we know that the release rate in creases when the effervescent increases but high amount of effervescent will cause the capsules to have too many big-sized bubbles and big sized. This would effect the dipping which would not be easy and consequently the capsule wall will be thick. The capsule and the body will therefore not fit adequately. Less than required amount of effervescent will produce small bubbles and the distribution will not be homogeneous. This will cause big standard deviation in the drug release rate. The optimal amount of effervescent should be between 0.5 to 2.5%.

EXAMPLE 1

To a 400 mL beaker was added 120 mL of distilled water and maintained at 80–85° C. on a water bath. 60 g of gelatin powder was slowly added with stirring until gelatin was totally dissolved to give the gelatin solution. The gelatin solution was cooled to 60° C. The capsules were prepared by No. 2 pin and mold which were previously pretreated with sun flower oil.

The pin and mold with a hole of 0.1–2.0 mm in diameter and the number of insertion from 1–20, were dipped into the gelatin solution and withdrawn slowly. After exposure to the air for 20 minutes, a knife was used to trim it. A special clip is then used to make insertions and subsequently detach the capsule produced.

After detaching, the capsules were exposed to formaldehyde for 2 hours and dried at 50° C. for 30 minutes to removed excess formaldehyde.

According to the formula, verapamil HCl: corn starch= 1:4, was used to fill the capsules and weighed. The dissolution profile using water as the dissolution is shown in FIG. 5.

EXAMPLE 2

To a 400 mL beaker was added 120 mL of distilled water and maintained at 80–85° C. on a water bath. 60 g of gelatin powder was slowly added with stirring until gelatin was totally dissolved to give the gelatin solution. The gelatin solution was cooled to 60° C.

Equal amount by weight of citric acid and $K_2CO_3$ were added (1 g, 2 g, and 4 g). Any bubble formed on the top of the gelatin solution was removed and No. 2 pin and mold which were previously pretreated with sun flower oil were used to prepare the capsules.

The pin and mold were dipped into the gelatin solution and withdrawn slowly. After which, they were exposed to air for 20 minutes and trimmed with knife. After detaching, the capsules were subjected to microwave treatment at 800 W for 1 minute to harden them and then filled with verapamil HCl: corn starch=1:4 (w/w). The dissolution profile using water as the dissolution is depicted in FIG. 6.

EXAMPLE 3

To a 400 mL beaker was added 120 mL of distilled water and maintained at 80–85° C. on a water bath. 60 g of gelatin powder was slowly added with stirring until gelatin was totally dissolved to give the gelatin solution. The gelatin solution was cooled to 60° C. The gelatin solution was purged with air for 10 seconds at a rate of 7.5 mL/second. The capsules were prepared by No. 2 pin and mold which were previously pretreated with sun flower oil. The pin and mold were dipped into the gelatin solution and withdrawn slowly, exposed to air for 20 minutes and trimmed. After detaching the capsules from pin and mold, Co-60 at 2 Mrad was used for the hardening process. Verapamil HCl: corn starch=1:4 (w/w) was used to fill the capsules and dissolution profile using water as the dissolution is shown in FIG. 7.

EXAMPLE 4

Capsules were prepared as described in Example 2. After detaching, the capsules were exposed to formaldehyde for 2 hours and dried at 50° C. for 30 minutes to remove excess formaldehyde.

According to the formula, Captopril: corn starch=1:4, was used to fill the capsules and weighed. The dissolution profile using water as the dissolution is shown in FIG. 8.

EXAMPLE 5

Capsules were prepared as described in Example 2. After detaching, the capsules were exposed to formaldehyde for 2 hours and dried at 50° C. for 30 minutes to remove excess formaldehyde.

According to the formula, Acetaminophen: corn starch= 1:4, was used to fill the capsules and weighed. The dissolution profile using water as the dissolution is shown in FIG. 8.

EXAMPLE 6

Capsules were prepared as described in Example 2. After detaching, the capsules were exposed to formaldehyde for 2 hours and dried at 50° C. for 30 minutes to remove excess formaldehyde.

According to the formula, Aspirin: corn starch=1:4, was used to fill the capsules and weighed. The dissolution profile using water as the dissolution is shown in FIG. 8.

EXAMPLE 7

Capsules were prepared as described in Example 2. After detaching, the capsules were exposed to formaldehyde for 2 hours and dried at 50° C. for 30 minutes to removed excess formaldehyde.

According to the formula, Diclofenac sodium: corn starch=1:4, was used to fill the capsules and weighed. The dissolution profile using water as the dissolution is shown in FIG. 8.

EXAMPLE 8

Capsules were prepared as described in Example 2. After detaching, the capsules were exposed to formaldehyde for 2 hours and dried at 50° C. for 30 minutes to remove excess formaldehyde.

According to the formula, nicardipine HCl: corn starch=1:2, was used to fill the capsules and weighed. The dissolution profile using water as the dissolution is shown in FIG. 8.

TABLE 1

The effects of exposure time of capsule to formalin on dissolution

| Exposure Time(hr) | Dissolution Time(hr) | Slope of Release(hr$^{-1}$) | Intercept of Release | $R^2$ | Release Exponent, n |
|---|---|---|---|---|---|
| 2 | 0.5–7 | 10.6 | 0.898 | 0.992 | 0.982 |
| 4 | 0.5–10 | 6.91 | −5.88 | 0.992 | 0.934 |
| 7 | 0.5–10 | 2.64 | −1.19 | 0.970 | 1.01 |

(Use water as dissolution medium, n = 6)

TABLE 2

The effects of exposure time of capsule to formalin on dissolution

| Exposure Time(hr) | Dissolution Time(hr) | Slope of Release(hr$^{-1}$) | Intercept of Release | $R^2$ | Release Exponent, n |
|---|---|---|---|---|---|
| 2 | 0.5–7 | 13.1 | 1.63 | 0.994 | 0.984 |
| 4 | 0.5–10 | 8.41 | −7.04 | 0.970 | 1.02 |

(Use 0.1N HCl solution as dissolution medium, n = 6)

TABLE 3

Values of effervescent added, dissolution time period, slope of release, intercept of release, coefficient of determination, and release exponent of various dissolution data

| Efferve-scent (%) | Dissolution Time(hr) | Slope of Release(hr$^{-1}$) | Intercept of Release | $R^2$ | n value of Korsmeyer |
|---|---|---|---|---|---|
| 0.1 | 0.5–10 | 7.63 | −5.36 | 0.995 | 1.24 |
| 1.01 | 0.5–10 | 8.82 | −6.75 | 0.975 | 1.14 |
| 2.17 | 0.5–10 | 10.6 | 0.898 | 0.992 | 0.982 |

I claim:

1. A method of producing a porous, controlled-release capsule comprising
    adding a gas generating agent to a gelatin solution to form a gelatin solution containing gas bubbles therein,
    forming a porous capsule from said gelatin solution containing gas bubbles therein,
    wherein said porous capsule has a plurality of holes in a wall of said capsule, and
    wherein said gas generating agent comprises a weak acid and a weak base.

2. The method of producing the porous, controlled-release capsule as defined in claim 1
    wherein said weak acid is a member selected from the group consisting of fumaric acid, citric acid, tartaric acid, and maleic acid, and
    wherein said weak base is a member selected from the group consisting of $K_2CO_3$, $Na_2CO_3$, $Li_2CO_3$, $CaCO_3$ and $MgCO_3$.

3. A method of producing a porous, controlled-release capsule comprising
    adding a gas generating agent to a gelatin solution to form a gelatin solution containing gas bubbles therein,
    forming a porous capsule from said gelatin solution containing gas bubbles therein,
    wherein said porous capsule has a plurality of holes in a wall of said capsule, and
    wherein said forming step further comprises
        hardening said porous capsule by either
            a) treating said porous capsule with a cross-linking reagent selected from the group consisting of methyl glycidyl ether, ethylene glycol diglycidyl ether, polyethylene glycol diglycidyl ether, glycerol polyglycidyl ether, polyglycerol polyglycidyl ether, formaldehyde, and glutaraldehyde, or
            b) exposing said porous capsule to ultraviolet light operating at 280–8000 mJ/cm$^2$, or
            c) exposing said porous capsule to microwaves operating at 400–1200 W for 0.1 to 20 minutes, or
            d) exposing said porous capsule to gamma-radiation or radiation emitted from Co-60 at an intensity of 1–5 Mrad.

4. A method of producing a porous, controlled-release capsule comprising introducing into a gelatin solution an inert substance which forms gas bubbles in said gelatin solution,
    forming a porous capsule from said gelatin solution containing gas bubbles therein,
    wherein said porous capsule has a plurality of holes in a wall of said porous capsule, and
    wherein said forming step further comprises
        hardening said porous capsule by either
            a) treating said porous capsule with a cross-linking reagent selected from the group consisting of methyl glycidyl ether, ethylene glycol diglycidyl ether, polyethylene glycol diglycidyl ether, glycerol polyglycidyl ether, polyglycerol polyglycidyl ether, formaldehyde, and glutaraldehyde, or
            b) exposing said porous capsule to ultraviolet light operating at 280–8000 mJ/cm$^2$, or
            c) exposing said porous capsule to microwaves operating at 400–1200 W for 0.1 to 20 minutes, or
            d) exposing said porous capsule to gamma-radiation or radiation emitted from Co-60 at an intensity of 1–5 Mrad.

5. A method of producing a porous, controlled-release capsule comprising
    dissolving gelatin powder in a heated water bath to form a gelatin solution, cooling said gelatin solution, dipping a pretreated pin and mold having from 1–20 insertions, wherein each of said insertions has a diameter of 0.1–2.0 mm, into said cooled gelatin solution, withdrawing said pin and mold from said gelatin solution to form a pin and mold having gelatin solution adhered thereto, exposing said pin and mold having gelatin solution adhered thereto to air to form a capsule, mechanically forming from 1–20 insertions in a wall of said capsule to form a porous capsule having holes with each of said holes being from 0.1–2.0 mm in diameter, detaching said porous capsule from said pin and mold, hardening said porous capsule by exposing said porous capsule to formaldehyde, and drying said exposed porous capsule.

6. A method of producing a porous, controlled-release capsule comprising dissolving gelatin powder in a heated water bath to form a gelatin solution, cooling said gelatin solution, adding citric acid and $K_2CO_3$ to said cooled gelatin solution to form a gelatin solution containing bubbles therein, dipping a pretreated pin and mold into said gelatin solution containing bubbles therein, withdrawing said pin and mold from said gelatin solution containing bubbles therein to form a pin and mold having adhered thereto said gelatin solution containing bubbles therein, exposing to air said pin and mold having adhered thereto said gelatin solution containing bubbles therein to form a porous capsule, detaching said porous capsule from said pin and mold, and hardening said porous capsule by exposing said porous capsule to microwaves or exposing said porous capsule to formaldehyde and drying.

7. A method of producing a porous, controlled-release capsule comprising dissolving gelatin powder in a heated water bath to form a gelatin solution, cooling said gelatin solution, introducing into said gelatin solution air to form bubbles in said gelatin solution, dipping a pretreated pin and mold into said gelatin solution containing bubbles therein, withdrawing said pin and mold from said gelatin solution containing bubbles therein to form a pin and mold having adhered thereto said gelatin solution containing bubbles therein, exposing to air said pin and mold having adhered thereto said gelatin solution containing bubbles therein to form a porous capsule, detaching said porous capsule from said pin and mold, and hardening said porous capsule by exposing said porous capsule to radiation emitted from Co-60.

* * * * *